US00RE42391E

(19) United States
(12) Reissued Patent
Wöhrle

(10) Patent Number: US RE42,391 E
(45) Date of Reissued Patent: May 24, 2011

(54) BIOROOT ENDOSSEOUS IMPLANT

(76) Inventor: Peter S. Wöhrle, Corona Del Mar, CA (US)

(21) Appl. No.: 10/366,531

(22) Filed: Feb. 12, 2003

Related U.S. Patent Documents

Reissue of:
(64) Patent No.: 6,283,754
Issued: Sep. 4, 2001
Appl. No.: 09/679,135
Filed: Oct. 3, 2000

U.S. Applications:
(63) Continuation of application No. 09/203,822, filed on Dec. 1, 1998, now Pat. No. 6,174,167.

(51) Int. Cl.
*A61C 8/00* (2006.01)

(52) U.S. Cl. ..... 433/173

(58) Field of Classification Search ..... 433/173, 433/172, 174, 175, 176, 223
See application file for complete search history.

(56) References Cited

U.S. PATENT DOCUMENTS

| | | | |
|---|---|---|---|
| 2,112,007 | A | 3/1938 | Adams |
| 3,849,887 | A | 11/1974 | Brainin |
| 4,051,598 | A | 10/1977 | Sneer |
| 4,416,629 | A | 11/1983 | Mozsary et al. |
| 4,468,200 | A | 8/1984 | Mnch |
| 4,624,673 | A | 11/1986 | Meyer |
| 4,713,003 | A | 12/1987 | Symington et al. |
| 4,812,120 | A | 3/1989 | Flanagan et al. |
| 4,856,994 | A | 8/1989 | Lazzara et al. |
| 4,960,381 | A | 10/1990 | Niznick |
| 5,004,422 | A | 4/1991 | Propper |
| 5,035,619 | A | 7/1991 | Daftary |
| 5,049,074 | A | 9/1991 | Otani et al. |
| 5,125,839 | A | 6/1992 | Ingber et al. |
| 5,246,370 | A | 9/1993 | Coatoam |
| 5,282,746 | A | 2/1994 | Sellers et al. |
| 5,310,343 | A | 5/1994 | Hasegawa et al. |
| 5,316,477 | A | 5/1994 | Calderon |
| 5,328,371 | A | 7/1994 | Hund et al. |
| 5,417,568 | A | 5/1995 | Giglio |

(Continued)

FOREIGN PATENT DOCUMENTS

| | | |
|---|---|---|
| CH | 413224 | 5/1966 |

(Continued)

OTHER PUBLICATIONS

Spiekerman, et al., "Implantology". Color Atlas of Dental Medicine, 1995, pp. 15, 22-23, 274-275, and 307.

(Continued)

*Primary Examiner* — Ralph A Lewis
(74) *Attorney, Agent, or Firm* — Knobbe Martens Olson & Bear, LLP

(57) ABSTRACT

The present invention relates to novel endosseous implants, which are designed so that the areas intended for bone soft tissue apposition exhibit a scalloped appearance, including both convex and concave patterns, to follow the naturally occurring bone morphology. Thus, the disclosed implants provide attachment possibilities for both bone and soft tissue, thereby effecting both hard- and soft-tissue preservation.

REEXAMINATION RESULTS

The questions raised in reexamination proceeding No. 90/007,836, filed Dec. 2, 2005, have been considered, and the results thereof are reflected in this reissue patent which constitutes the reexamination certificate required by 35 U.S.C. 307 as provided in 37 CFR 1.570(e) for *ex parte* reexaminations, or the reexamination certificate required by 35 U.S.C. 316 as provided in 37 CFR 1.997(e) for *inter partes* reexaminations.

105 Claims, 6 Drawing Sheets

U.S. PATENT DOCUMENTS

| | | | |
|---|---|---|---|
| 5,417,569 | A | 5/1995 | Perisse |
| 5,431,567 | A | 7/1995 | Daftary |
| 5,458,488 | A | 10/1995 | Chalifoux |
| 5,464,440 | A | 11/1995 | Johansson |
| 5,527,182 | A | 6/1996 | Willoughby |
| 5,584,693 | A | 12/1996 | Nishihara |
| 5,588,838 | A | 12/1996 | Hansson et al. |
| 5,622,500 | A | 4/1997 | Niznick |
| 5,636,989 | A | 6/1997 | Somborac et al. |
| 5,667,384 | A | 9/1997 | Sutter et al. |
| 5,674,069 | A | 10/1997 | Osorio |
| 5,695,334 | A | 12/1997 | Blacklock et al. |
| 5,759,034 | A | 6/1998 | Daftary |
| 5,779,480 | A | 7/1998 | Groll et al. |
| 5,876,454 | A | 3/1999 | Nanci et al. |
| 5,908,298 | A | 6/1999 | Dürr et al. |
| 5,931,675 | A | 8/1999 | Callan |
| 5,989,027 | A | 11/1999 | Wagner et al. |
| 5,989,029 | A | 11/1999 | Osorio et al. |
| 6,012,923 | A | 1/2000 | Bassett et al. |
| 6,024,567 | A | 2/2000 | Callan |
| 6,142,782 | A | 11/2000 | Lazarof |
| 6,162,054 | A | 12/2000 | Takacs |
| 6,164,969 | A | 12/2000 | Dinkelacker |
| 6,174,167 | B1 | 1/2001 | Wöhrle |
| 6,217,331 | B1 | 4/2001 | Rogers et al. |
| 6,217,333 | B1 | 4/2001 | Ercoli |
| 6,227,858 | B1 | 5/2001 | Lundgren |
| 6,231,342 | B1 | 5/2001 | Osorio et al. |
| 6,273,720 | B1 | 8/2001 | Spalten |
| 6,280,195 | B1 | 8/2001 | Broberg et al. |
| 6,283,753 | B1 | 9/2001 | Willoughby |
| 6,283,754 | B1 | 9/2001 | Wöhrle |
| 6,287,115 | B1 | 9/2001 | Lustig et al. |
| 6,312,260 | B1 | 11/2001 | Kumar et al. |
| 6,350,126 | B1 | 2/2002 | Levisman |
| 6,364,663 | B1 | 4/2002 | Dinkelacker |
| 6,431,867 | B1 | 8/2002 | Gittelson et al. |
| 6,464,500 | B1 | 10/2002 | Popovic |
| 6,527,554 | B2 | 3/2003 | Hurson et al. |
| 6,547,564 | B1 | 4/2003 | Hansson |
| 6,619,958 | B2 | 9/2003 | Beaty et al. |
| 6,626,911 | B1 | 9/2003 | Engman et al. |
| 6,652,765 | B1 | 11/2003 | Beaty |
| 6,655,961 | B2 | 12/2003 | Cottrell |
| 6,672,872 | B2 | 1/2004 | Cottrell |
| 6,854,972 | B1 | 2/2005 | Elian |
| 6,939,135 | B2 | 9/2005 | Sapian |
| 7,270,542 | B2 | 9/2007 | Cottrell |
| 2001/0021498 | A1 | 9/2001 | Osorio et al. |
| 2002/0182567 | A1 | 12/2002 | Hurson et al. |
| 2003/0031981 | A1 | 2/2003 | Holt |
| 2003/0031982 | A1 | 2/2003 | Abarno |
| 2003/0068599 | A1 | 4/2003 | Balfour et al. |
| 2003/0124489 | A1 | 7/2003 | Hurson et al. |
| 2005/0014108 | A1 | 1/2005 | Wohrle et al. |
| 2005/0214714 | A1 | 9/2005 | Wohrle |
| 2006/0188846 | A1 | 8/2006 | Wohrle et al. |
| 2006/0194170 | A1 | 8/2006 | Wohrle et al. |
| 2006/0246398 | A1 | 11/2006 | Groll et al. |

FOREIGN PATENT DOCUMENTS

| | | | |
|---|---|---|---|
| DE | 250 052 | A1 | 9/1987 |
| DE | 250052 | A1 | 9/1987 |
| DE | 43 39 060 | A1 | 9/1993 |
| EP | 0 705 574 | A2 | 4/1996 |
| EP | 0 820 737 | A2 | 1/1998 |
| EP | 0 868 889 | A1 | 10/1998 |
| EP | 0879580 | | 11/1998 |
| EP | 1 013 236 | | 12/1998 |
| EP | 0 910 297 | | 10/2001 |
| FR | 2634369 | | 7/1988 |
| FR | 2 317 904 | | 2/1997 |
| GB | 1291470 | | 10/1972 |
| IT | 540713 | | 3/1956 |
| JP | 125260 | | 5/1988 |
| JP | 08-117250 | | 5/1996 |
| JP | 10-033562 | | 2/1998 |
| WO | WO 96/29020 | | 9/1996 |
| WO | WO 97/37610 | | 10/1997 |
| WO | WO 98/23221 | | 6/1998 |
| WO | WO 98/42273 | | 10/1998 |
| WO | WO 00/32124 | | 6/2000 |
| WO | WO 00/47127 | | 8/2000 |
| WO | WO 01/049199 | A3 | 7/2001 |
| WO | WO 01/50972 | A2 | 7/2001 |
| WO | WO 03/000909 | | 1/2003 |
| WO | WO 03/005928 | A1 | 1/2003 |
| WO | WO 03/028576 | | 4/2003 |
| WO | WO 03/059189 | | 6/2003 |

OTHER PUBLICATIONS

Dinkelacker, Wolfgang, "Vergleighende Untersuchung zur Passform metallkeramischer Kronen auf gegossener und galvanish hergestellter metallener Substruktur" Medizinischen Fakultat (Klinische Medizin) der Eberhard-Karls-Universitat Tubingen, 1990.

Straumann Dental—Brochure; May 2000.

Supplemental Search Report for European Application No. 99 96 8057 (European Counterpart of the current application), mailed Mar. 30, 2005.

Parel, et al., "Esthetics and Osseointegration", 1989. p. 36, 40, 41, and 121.

Request for Ex Parte Reexamination of US Patent No. 6,283,754 (U.S. Appl. No. 90/007,836).

Appendix A to Request for Reexamination of US Patent No. 6,283,754.

Appendix B to Request for Reexamination of US Patent No. 6,283,754.

Appendix C to Request for Reexamination of US Patent No. 6,283,754.

Appendix D to Request for Reexamination of US Patent No. 6,283,754.

Appendix E to Request for Reexamination of US Patent No. 6,283,754.

Appendix F to Request for Reexamination of US Patent No. 6,283,754.

Appendix G to Request for Reexamination of US Patent No. 6,283,754.

Appendix H to Request for Reexamination of US Patent No. 6,283,754.

Order Granting Request For Ex Parte Reexamination (U.S. Appl. No. 90/007,836).

Albrektsson et al. "Osseointegrated Dental Implants", The Dental Clinics of North America, vol. 30 No. 1, Jan. 1986. p. 151-174.

Eckert et al. "Patient Evaluation and Prosthodontic Treatment Planning for Osseointegrated Implants", The Dental Clinics of North America, vol. 33 No. 4, Oct. 1989. p. 599-618.

Hobo et al. "Osseointegration and Occlusal Rehabilitation", 1989. p. 3-7.

Misch "Implant Terminology" Contemporary Implant Dentistry, 1993. p. 19-27.

Spierkermann et al. "Implant Systems" Color Atlas of Dental Medicine: Implantology, 1995. p. 25-58.

Examination Report received in corresponding European Patent Application No. 99968057.2, mailed Apr. 21, 2009, 5 pages.

Brånemark, P.I. et al., *Osseointegrated Implants In The Treatment Of The Edentulous Jaw. Experience From A 10-Year Period,* Scand. J. Plastic Reconstruc. Surg., (1977) (Suppl. 16 at p. 9); Almqvist & Wiksell International, Stockholm, Sweden.

Lefkove, Michael, D., et al., *Immediate Loading of Cylinder Implants With Overdentures in the Mandibular Symphysis: The Titanium Plasma-Sprayed Screw Technique,* J. Oral Implant. (1990); 16:265-271; Allen Press, Lawrence, Kansas.

Buser, D., et al., *Influence of Surface Characteristics on Bone Integration of Titanium Implants. A Histomorphometric Study In Miniature Pigs,* J. Biomed. Materials Res., (1991); 25:889-902; John Wiley & Sons, Hoboken, New Jersey.

Zablotsky, M., et al., *Histological And Clinical Comparisons Of Guided Tissue Regeneration On Dehisced Hydroxyapatite-Coated And Titanium Endosseous Implant Surfaces: A Pilot Study,* Int. J Oral Maxillofac. Implants. (1991); 3:294-303; Quintessence Publishing Co., Inc., Carol Stream, Illinois.
Gottlander, M., et al., *Histomorphometric Analyses Of Hydroxyapatite-Coated And Uncoated Titanium Implants. The Importance of The Implant Design.,* Clin. Oral Implants Res. (1992); 2:71-76; Blackwell Publishing Ltd., Oxford, United Kingdom.
Gotfredsen, K., et al., *Histomorphometric And Removal Torque Analysis For $TiO_2$-Blasted Titanium Implants—An Experimental Study On Dogs,* Clin. Oral Impl. Res. (1992); 3:77-84; Copenhagen, Denmark.
Schwartz, Z., et al., *Underlying Mechanisms at the Bone-Surface Interface During Regeneration,* J. Periodont. Res. (1992); 32: 166-171; Blackwell Publishing Ltd., Oxford, United Kingdom.
Wagner, W., *A Brief Introduction To Advanced Surface Modification Techniques,* J. Oral Implant., (1992); 18:231-235; Allen Press, Lawrence, Kansas.
Wismeijer, D., et al., *Patient Satisfaction With Overdentures Supported by One-Stage TPS Implants,* Int J. Oral Maxillofac. Implants. (1992); 1: 51-55; Quintessence Publishing Co., Inc., Carol Stream, Illinois.
Cook, S., et al., *The Effect Of Surface Macrotexture On The Mechanical and Histologic Characteristics Of Hydroxyapatite-Coated Dental Implants,* J. Oral Implant. (1993); 4:288-294; Allen Press, Lawrence, Kansas.
Wennerberg, A., et al., *Design and Surface Characteristics of 13 Commercially Available Oral Implant Systems,* Int. J. Oral Maxillofac. Implants (1993); 8:622-633; Quintessence Publishing Co., Inc., Carol Stream, Illinois.
Olefjord, I., et al., *Surface Analysis of Four Dental Implant Systems,* Int. J. Oral Maxillofac. Implants (1993); 8:32-40; Quintessence Publishing Co., Inc., Carol Stream, Illinois.
Spiekermann, H., et al., *A 10-Year Follow-Up Study of IMZ and TPS Implants In The Edentulous Mandible Using Bar-Retained Overdentures,* Int. J. Oral Maxillofac. Implants (1995); 10:231-243; Quintessence Publishing Co., Inc., Carol Stream, Illinois.
Wennerberg, A., et al., *A Histomorphometric And Removal Torque Study Of Screw-Shaped Titanium Implants With Three Different Surface Topographies,* Clin. Oral. Implant. Res. (1995); 6:24-30; Quintessence Publishing Co., Inc., Carol Stream, Illinois.
Gotfredsen, K, et al., *Anchorage of $TiO_2$-Blasted, HA Coated, and Machined Implants: An Experimental Study With Rabbits.* J. Biomed. Materials Res. (1995); 29:1223-1231; John Wiley & Sons, Hoboken, New Jersey.
Cochran, D.L., et al., *Evaluation of an Endosseous Titanium Implant with a Sandblasted and Acid-Etched Surface in the Canine Mandible: Radiographic Results,* Clin. Oral Impl. Res. (1996); 7:240-252; Blackwell Publishing Ltd., Oxford, United Kingdom.
Wennerberg, A., et al., *Torque And Histomorphometric Evaluation Of C.P. Titanium Screws Blasted With 25- and 75-Microns-Sized Particles Of $Al_2O_3$,* J Biomed. Materials Res. (1996) 2:251-60; John Wiley & Sons, Hoboken, New Jersey.
Wennerberg, A., et al., *Bone Tissue Response To Commercially Pure Titanium Implants Blasted With Fine And Coarse Particles Of Aluminum Oxide.,* Int. J. Oral Maxillofac. Implants (1996) 1:38-45; Quintessence Publishing Co., Inc., Carol Stream, Illinois.
Klokkevold, P., et al., *Osseointegration Enhanced by Chemical Etching of The Titanium Surface—A Removal Torque Study in the Rabbit,* Clin. Oral Impl. Res.(1997); 8:442-447; Blackwell Publishing Ltd., Oxford, United Kingdom.
Wennerberg, A., et al., *A 1-Year Follow-Up Of Implants Of Differing Surface Roughness Placed in Rabbit Bone.,* Int. J. Oral Maxillofac. Implants (1997); 4:486-494; Quintessence Publishing Co., Inc., Carol Stream, Illinois.
Cochran, D.L., et al., *Bone Response to Unloaded and Loaded Titanium Implants with a Sandblasted and Acid-etched Surface: A Histometric Study in the Canine Mandible,* J. Biomed. Materials res., (1997); 40:1-11; John Wiley & Sons, Hoboken, New Jersey.
Piattelli, A., et al., *Immediate Loading of Titanium plasma-Sprayed Screw-Shaped Implants in Man: A Clinical and Histological Report of Two Cases,* J. Periodontol. (1997); 68:591-597; Chicago, Illinois.
Hansson, Stig, et al., *The Relation Between Surface Roughness and Interfacial Shear Strength for Bone Anchored Implants—A Biomechanical Approach in Towards an Optimized Dental Implant and Implant Bridge Design—A Biomechanical Approach,* Biomechanics, Department of Polymeric Materials, School of Mechanical and Vehicular Engineering, Chalmers University of Technology, Göteborg, Sweden (1997).
Gottlander, M., et al., *Short- and Long-Term Animal Studies With A Plasma-Sprayed Calcium Phosphate-Coated Implant,* Clin. Oral Implants Res. (1997); 5:345-351; Blackwell Publishing Ltd., Oxford, United Kingdom.
Bolind, P., et al., *Influence Of External Administration Of Epinephrine On Bone Regeneration.,* Int. J. Oral Maxillofac Implants. (1989); 4:285-287; Quintessence Publishing Co., Inc., Carol Stream, Illinois.
Najjar, T.A., et al., *Enhanced Osseointegration Of Hydroxylapatite Implant Material,* Oral Surg. Oral Med Oral Pathol. (1991) 1:9-15; Dept. of Oral Pathology, UMD—New Jersey Dental School, Newark, NJ.
Zablotsky, M., et al., *The Macroscopic, Microscopic And Spectrometric Effects Of Various Chemotherapeutic Agents On The Plasma-Sprayed Hydroxyapatite-Coated Implant Surface,* Clin. Oral Implants Res. (1992); 4:189-98; Blackwell Publishing Ltd., Oxford, United Kingdom.
Zablotsky, M., et al., *Hydroxyapatite Coatings In Implant Dentistry,* Implant Dent. (1992); 4:253-257; Lippincott, Williams & Wilkins, Hagerstown, Maryland.
Zablotsky, M., *HA Coatings In Implant Dentistry: Hype, Hysteria, Or Clinical Reality?,* Pract. Periodontics Aesthet. Dent. (1994); 2:60-65; USA.
Strub et al., "The Re Implant® System for Immediate Implant Placement". Journal of Esthetic Dentistry 1997, vol. 9, pp. 187-196.
Kohal et al., "Custom-made root analogue titanium implants placed into extraction sockets". Clinical Oral Implants Research 1997, vol. 8, pp. 386-392.
Heydecke et al., "Optimal Esthetics in Single Tooth Replacement with the Re-implant System: A Case Report". The International Journal of Prosthodontics 1999, vol. 12, pp. 184-189.
Gieloff et al., "Bio-Design-Implatantate Soforimplantate mit dem Re Implant System", ZWR, 104. Jahrg. 1995, Nr. 4, pp. 252-256.
Kohal et al., "Wurzelanaloge Titanimplantate (Bio-Design-Implantate) für die Sofortimplantation-Das Re-implant-System". Implantologie 1996, vol. 2, pp. 99-115 (with English Translation).
Product brochure published before Dec. 1, 1998.
Baier, et al., "Future Directions in Surface Preparation of Dental Implants", Journal of Dental Education, 52:788-791.
Bengazi, et al., 1996, "Recession of the soft tissue margin at oral implants", *Clinical Oral Implants Research,* 7:303-310.
Branemark, et al., 1985, "Tissue-Integrated Prosthesis: Nature and Significance of the Edentulous State" Quintessence Publishing Co., Inc., chapter 2:77-88.
Brunski, John B., 1988, Blomechanics of Oral Implants: Future Research Directions, Journal of Dental Education, 52:775-787.
Buser, et al., 1991, "Tissue Integration of One-Stage ITI Implants: 3 year Results of a Longitudinal Study With Hollow-Cylinder and Hollow-Screw Implants.", The International Journal of Oral & Maxillofacial Implants, 6:405-412.
Buser, et al., 1996m "Comparison of healed tissues adjacent to submerged and non-submerged unloaded titanium dental implants", Clinical Oral Implants Research, 7:11-19.
Chiche, el al., 1998, "Multidisplinary Implant Dentistry for improved Aesthetics and Function", Pract Periodont. Aesthet. Dent., 10:177-186.
Gieloff et al., 1995, Bio-Design-Implantate Sofortimplantate mit dem Re Implant System, p. 252-256 ( with English translation).
Gomez-Roman, et al., 1997, "The Frialit-2 Implant System: Five-Year Clinical Experience in Single-Tooth and Immediately Postextraction Applications", The International Journal of Oral & Maxillofacial Implant, 12:299-309.
Jansen, et al., 1997, "Microbial Leakage and Marginal Fit of the Implant-Abutment Interface", The International Journal of Oral & Maxillofacial Implants, 12:527-540.
Kirsch, et al., 1989., "The IMZ Osteointegrated Implant System", Dental Clinics of North America, 33:733-791.

Kohal et al., 1996., "Wurzetanagoge Titanimplantate (Bio-Design-Implantate) für die Sofortimplatnation-Das Re-Implant®-System", p. 99-115 (with English Translation).
Krauser, Jack T., 1989., "Hydorxylapatite-Coated Dental Implants", Dental Clinics of North America, 33:879-903.
Langer, et al., 1993, "The Wide Fixture: A Solution for Special Bone Situations and a Rescue for the Compromised Implant. Part 1", *The International Journal of Oral & Maxillofacial Implants,* 8:400-408.
Meffert, Roland M., DDS, 1988, "The Soft Tissue Interface in Dental Implantology", Journal of Dental Education, 52:810-878.
Niznick, Gerald A., Oct. 1989, "A Multimodal Approach to Implant Prosthodontics", Dental Clinics of North America, 33:869-878.
Olsson, et al., 1995, "MkII—A Modified Self-Tapping Branemark Implant: 3-Year Results of a Controlled Prospective Pilot Study", The International Journal of Oral & Maxillofacial Implant, 10:15-21.
Prestipino, et al., Jan./Feb. 1993, "esthetic High-Strength Implant Abutments. Part 1", Journal of Esthetic Dentistry, p. 29-35.
W. Eugene Roberts, DDS, Ph.D., 1998, "Bone Tissue Interface", Journal of Dental Education, 52:804-809.
Saadoun, et al., 1998, "Peridontal Implications in Implant Treatment Planning of Aesthtic Results", Pract. Periodont. Asthet. Dent., 10:655-664.
Schnitman, et al., 1988, Implants for Partial Edentulism, Journal of Dental Education, 52:725-736.
Siegeie, et al., 1989, "Numerical Investigations of the Influence of Implant Shape on Stress Distribution in the Jaw Bone", the International Journal of Oral & maxillofacial Implants, 4:333-340.
Sullivan, et al., May/Jun. 1993, "Considerations for Successful Single tooth Implant Restorations", Journal of Esthetic Dentistry, 5:119-124.
Wennerberg, et al., "Design and Surface Characteristics of 13 Commercially Available Oral Implant Systems", International Journal of Oral & Maxillofacial Implants, 8:622-633.
F.A. Young, D.Sc., 1988, "Future Directions in Dental Implants Materials Research", Journal of Dental Education 52:770-774.
Wennerberg et al., "Experimental study of turned and grit-blasted screw-shaped implants with special emphasis on effects of blasting material and surface topography", 1996.
Coatoam, Gary W. et al., "Immediate Placement of Anatomically Shaped Dental Implants". Journal of Oral Implantology, vol. 26, No. 3/2000, p. 170-176, 2000.
Coatoam, Gary W., "Indirect Sinus Augmentation Procedures Using One-Stage Anatomically Shaped Root-form Implants". Journal of Oral Implantology, vol. 23, No. 1 & 2/1997, p. 25-42, 1997.
Coatoam, Gary W. et al., "A Four-year Study Examining the Results of Indirect Sinus Augmentation Procedures". Journal of Oral Implantology, vol. 23, No. 3/1997, pp. 117-127, 1997.
Coatoam, Gary W. et al., "The Segmental Ridge-Split Procedure". J Periodontal, vol. 74, No. 5, May 2003, p. 757-770.
Wennerberg, A; T. Albrektsson; B. Andersson; *Design and Surface Characteristics of 13 Commercially Available Oral Implant Systems;* Int'l J. of Oral & Maxillofacial Implants; 6:622-633 (1993); Quintessence Publishing, Hanover Park, IL, USA.
Wennerberg, A.; *On Surface Roughness and Implant Incorporation;* Dept. Biomaterials & Handicap Research, Institute for Surgical Sciences, Dept. of Prosthetic Dentistry, Göteborg University, Göteborg, Sweden (1996).
Wennerberg, A.; T. Albrektsson; B. Andersson; J. J. Krol; *A Histomorphometric and Removal Torque Study of Screw-Shaped Titanium Implants with Three Different Surface Topographies;* Clinical Oral Implants Research; 6:24-30 (1995), Blackwell Munksgaard, Frederiksberg C, Denmark.
Baier, et al., 1988, "Future Directions in Surface Preparation of Dental Implants", *Journal of Dental Education,* 52:788-791.
Brånemark, et al., 1985, "Tissue-Integrated Prostheses", *Quintessence Publishing Co., Inc.,* p. 11-76.
John B. Brunski, 1988, "Biomechanics of Oral Implants: Future Research Directions", *Journal of Dental Education,* 52:775-787.
Buser, et al., 1991, "Tissue Integration of One-Stage ITI Implants: 3-Year Results of a Longitudinal Study With Hollow-Cylinder and Hollow-Screw Implants", *The International Journal of Oral & Maxillofacial Implants,* 6:405-412.
Buser, et al., 1996, "Comparison of healed tissues adjacent to submerged and non-submerged unloaded titanium dental implants", *Clinical Oral Implants Research,* 7:11-19.
Chiche, et al., 1998, "Multidispilinary Implant Dentistry for Improved Aesthetics and Function", *Pract Periodont. Aesthet. Dent.,* 10:177-186.
Gomez-Roman, et al., 1997, "The Frialit-2 Implant System: Five-Year Clinical Experience in Single-Tooth and Immediately Postextraction Applications", *The International Journal of Oral & Maxillofacial Implants,* 12:299-309.
"Implantatsysteme und ihre Komponenten", 1998, *Implantologie,* 1:75-79.
Jansen, et al., 1997, "Microbial Leakage and Marginal Fit of the Implant-Abutment Interface", *the International Journal of Oral & Maxillofacial Implants,* 12:527-540.
Kirsch, et al., 1989., "The IMZ Osteointegrated Implant System", *Dental Clinics of North America,* 33:733-791.
Jack T. Krauser, DMD, Oct. 1989, "Hydroxylapatite-Coated Dental Implants", *Dental Clinics of North America,* 33:879-903.
Roland M. Meffert, DDS, 1988, "The Soft Tissue Interface in Dental Implantology", *Journal of Dental Education,* 52:810-811.
Gerald A. Niznick, Oct. 1989, "A Multimodal Approach to Implant Prosthodontics", *Dental Clinics of North America,* 33:869-878.
Olsson, et al., 1995, "MkII—A Modified Self-Tapping Brånemark Implant: 3-Year Results of a Controlled Prospective Pilot Study", *The International Journal of Oral & Maxillofacial Implant,* 10:15-21.
Prestipino, et al., Jan./Feb. 1993, "Esthetic High-Strength Implant Abutments. Part 1",*Journal of Esthetic Dentistry,* p. 29-35.
W. Eugene Roberts, DDS, Ph.D., 1998, "Bone Tissue Interface", *Journal of Dental Education,* 52:804-809.
Saadoun, et al., 1998, "Periodontal Implications in Implant Treatment Planning for Aesthetic Results", *Pract. Periodont. Aesthet. Dent.,* 10:655-664.
Schnitman, et al., 1988, "Implants for Partial Edentulism", *Journal of Dental Education,* 52:725-736.
Siegele, et al., 1989, "Numerical Investigations of the Influence of Implant Shape on Stress Distribution in the Jaw Bone", *The International Journal of Oral & Maxillofacial Implants,* 4:333-340.
Sullivan, et al., May/Jun. 1993, "Considerations for Successful Single Tooth Implant Restorations", *Journal of Esthetic Dentistry,* 5:119-124.
Wennerberg, et al., 1993, "Design and Surface Characteristics of 13 Commercially Available Oral Implant Systems", *International Journal of Oral & Maxillofacial Implants,* 8:622-633.
F.A. Young, D.Sc., 1988, "Future Directions in Dental Implants Materials Research", *Journal of Dental Education,* 52:770-774.

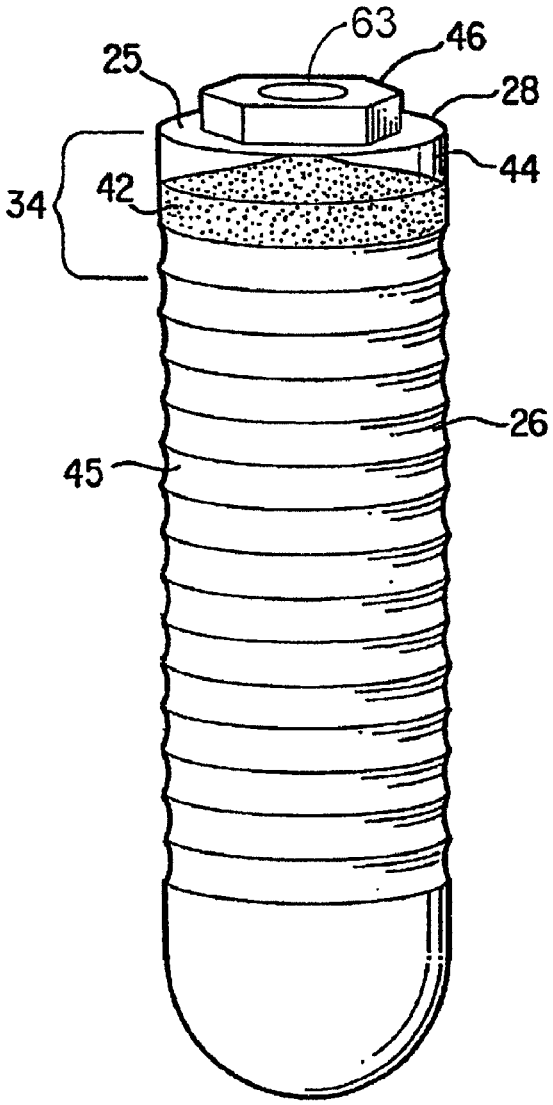
FIG. 5B [AMENDED]
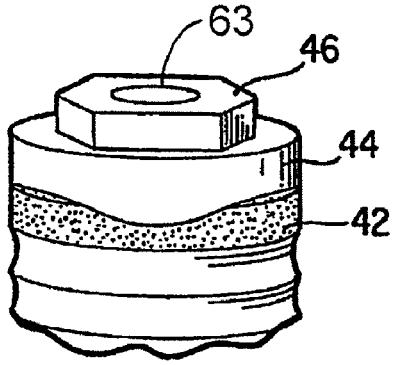
FIG. 5A [AMENDED]

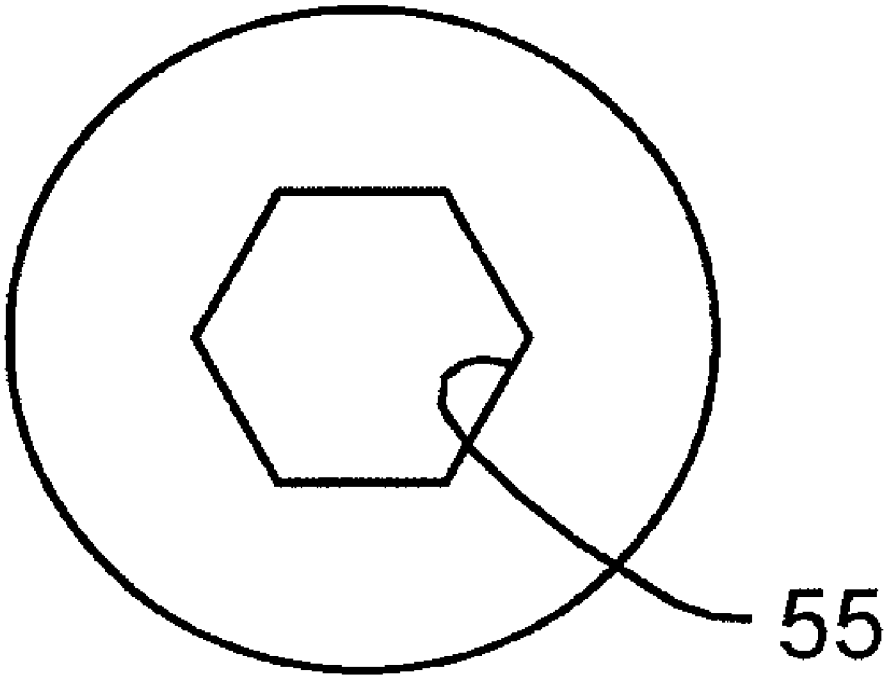
FIG. 5C [NEW]

FIG. 8 [AMENDED]

BIOROOT ENDOSSEOUS IMPLANT

Matter enclosed in heavy brackets [ ] appears in the original patent but forms no part of this reissue specification; matter printed in italics indicates the additions made by reissue.

This is a continuation of application Ser. No. 09/203,822, filed Dec. 1, 1998, U.S. Pat. No. 6,174,167.

FIELD OF INVENTION

The present invention relates generally to the field of implant dentistry, and more particularly to the design of one- and two-stage endosseous implants.

BACKGROUND OF THE INVENTION

Endosseous, i.e., intra boney, implants are commonly used to support fixed or removable prostheses where a patient's natural roots have been lost, and as a consequence, support is lacking to provide an adequate foundation onto which the dentist can rebuild a dentition. As the aging population retains more of their natural teeth, and as the younger generations want to take advantage of more conservative approaches offered by implant dentistry, e.g, using a single implant rather than cutting down adjacent teeth to support a short span bridge to replace a missing tooth, implant dentistry has gained more and more popularity and has moved into the mainstream of dentists worldwide.

The current implant design is based on an endosseous fixture, a titanium screw that acts as an artificial root: Brånemark, Tissue-Integrated Prostheses (1985). Modifications made to the endosseous fixture have centered on the macro structure of the implant (e.g., by exchanging the screw with a press-fit/cylindrical implant, a stepped screw or cylinder, or a tapered screw or cylinder), (Brunski J. B., Biomechanics Of Oral Implant,. Future Research Directions NIH Consensus Development Conference on Dental Implants, 1988; Kirsch A. et al., The IMZ Osseointegrated Implant System, Dent. Clin. North Am. 1989 (4), 33:733-791; Nimick G. A., A Multimodal Approach To Implant Prosthodontics, Dent. Clin. North Am. 1989(4), 33:869-878; Wennerberg A. et al., Design And Surface Characteristics Of 13 Commercially Available Oral Implant Systems, Id. 1993:8:622-633; Siegele D. et al., Numerical Investigations Of The Influence Of Implant Shape On Stress Distribution In The Jaw Bone, Id., 1989:4:333-340; Olsson M. et al., MkII-a Modified Self-Tapping Brånemark Implant: 3-Year Results, Id. at 1995:10: 15-21; Langer B. et al., The Wide Fixture: A Solution For Special Bone Situations And A Rescue For The Compromised Implant, Part 1, Id., 1993:8:400-408; Schnitman P. A. et al., Implants For Partial Edentulism, NIH Consensus Development Conference On Dental Implants, 1988), on the micro structure (e.g., surface modifications such as use of machined titanium, blasted titanium, titanium alloy, acid-etched titanium, plasma-sprayed titanium and hydroxyappatite coating such as growth factors and proteins), (Baier R. E. et al., Future Directions In Surface Preparation Of Dental Implants, NIH Consensus Development Conference On Dental Implants, 1988; Young F. A., Future Directions In Dental Implant Materials Research, Id.; Krauser J., Hydroxylappatite-Coated Dental Implants, Dent. Clin. North Am. 1989, 33:4:879-903; Buser D. et al., Tissue Integration Of One-Stage ITI Implants: 3-Year Results Of A Longitudinal Study With Hollow-Cylinder And Hollow-Screw Implants, Int. J. Oral Maxillofac. Implants, 1991:6:405-412), on one-vs-two-stage designs, (Weber H. P. et al., Comparison Of Healed Tissues Adjacent To Submerged And Non-Submerged Unloaded Titanium Dental Implants, Clin. Oral Impl. Res. 1996:7:11-19; Busser D. et al., Tissue Integration Of One-Stage ITI Implants: 3-Year Results Of A Longitudinal Study With Hollow-Cylinder and Hollow-Screw Implants, Int. J. Oral Maxillofac Implants 1991:6:405-412), and on modifying the connection between the implant and its abutment (e.g., either internal hex, external hex, standard hex, tall hex, wide hex, etc.), (U.S. Pat. No. 4,960,381; U.S. Pat. No. 5,407,359; U.S. Pat. No. 5,209,666; U.S. Pat. No. 5,110,292).

Irrespective of the design variables discussed above, current systems have two general characteristics in common: First, the abutment-implant interface is planar; and second, the area intended for bone apposition, i.e., osseointegration, terminates parallel to the abutment-implant interface, 360 degrees around the implant.

Traditionally, endosseous implants were designed for treatment of the fully edentulous patient. In general, this particular patient population exhibits reduced bone-tissue volume, both in height and width when compared to the partially edentulous patient with recent or impending tooth loss. However, the bone-tissue morphology of partially edentulous patients significantly differs from that of fully edentulous patients, in that the naturally occurring supporting bone structures reveal a scalloped architecture around the tooth.

Currently available implant technology does not take the different bone-tissue morphologies into consideration. Heretofore use of an implant with an intended bone-tissue apposition surface parallel to a flat abutment-implant interface has led to either (1) placement of soft-tissue intended parts of the implant within bone-tissue, leading to bone-tissue resorption in these areas, and/or (2) exposure of hard-tissue intended surfaces to the soft tissue, resulting in possible peri-implant infections due to bacterial colonization around the rough surface and potential loss of the implant.

SUMMARY OF THE INVENTION

The present invention is directed towards novel endosseous implants, which are structured to better maintain hard and soft-tissue in the area where the implant exits from the bone-tissue and transverses the soft-tissue. More particularly, the implants of the present invention are designed so that areas intended for hard- and soft-tissue apposition exhibit a scalloped appearance, including convex and/or concave patterns, which approximate the naturally occurring bone morphology. Thus, the implants of the present invention provide substantially increased attachment possibilities for both bone-tissue and soft-tissue, thereby facilitating bone-tissue and soft-tissue preservation and maintenance.

The present invention will enable the surgeon to place an implant into residual bone with the surface of the implant intended for bone-tissue contact and apposition (machined or roughened, surface coated or textured, altered with biologic modifiers such as proteins and growth factors, or any combination thereof) being substantially in contact with bone-tissue, and with the surface intended for soft-tissue apposition (polished/treated with soft tissue specific surface modifications) being substantially in contact with soft-tissue.

More specifically, the implant, according to an embodiment of the present invention, is a substantially cylindrical shaft made from a biocompatible material having a distal end and a proximal end. A bone-tissue/soft-tissue transition region and a abutment-implant interface are both disposed towards the proximal end of the shaft. The bone-tissue/soft-tissue transition region is defined as the approximate region of the shaft and/or the abutment-implant interface where the implant exits the bone-tissue and transverses into the soft-tissue. The bone-tissue/soft-tissue transition region has a bone-tissue apposition surface configured to approximate the physiological contours of the alveolar bone. In a two-stage implant, the abutment-implant interface may be either substantially planar, approximately 90° to the longitudinal axis of the shaft, or contoured to approximate the contour of the alveolar bone. In a one-stage implant the abutment is permanently attached to the abutment-implant interface, or an integral part of the implant itself. The abutment, in both one-and two-stage implants, has an abutment-crown interface, which is either substantially planar or contoured to approximate the contour of the alveolar bone, and a chimney onto which the crown is secured.

An implant constructed according to the principles of the present invention facilitates hard- and soft-tissue maintenance, increases longevity of the implant and improves its aesthetic appearance. As will be readily apparent to the skilled artisan, the present invention may be applied to numerous prosthetic applications, such as, but not limited to, a single tooth replacement, an abutment for a bridge (fixed partial denture) regardless of the nature of the other abutment (natural tooth or implant), a pier abutment or an over denture abutment.

BRIEF DESCRIPTION OF THE DRAWINGS

FIG. 5A depicts a three-dimensional top frontal view of the implant in FIG. 3;

FIG. 5B depicts a three-dimensional interproximal top view of the implant in FIG. 3

*FIG. 5C is a top view of an embodiment of an implant with an internal hex connection.*

DETAILED DESCRIPTION OF THE PREFERRED EMBODIMENTS

Figure 1:
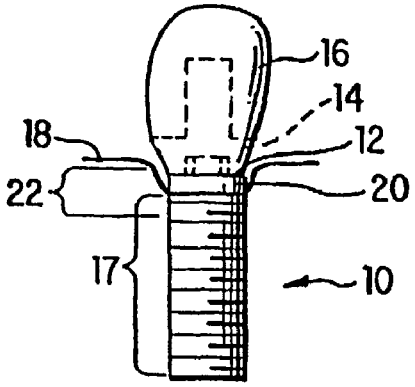
FIG. 1 (PRIOR ART)
FIG. 1 depicts a frontal view of a prior art implant.
Figure 2:
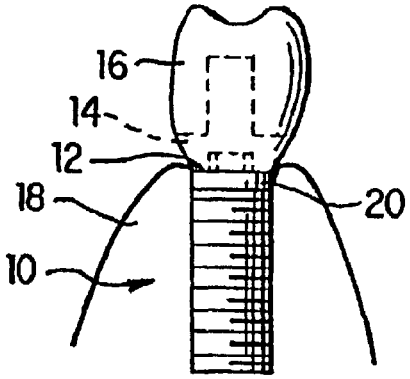
FIG. 2 (PRIOR ART)
FIG. 2 depicts an interproximal view of the prior art implant in FIG. 1.

FIGS. 1 and 2 show prior art implant 10, abutment-implant interface 12, abutment 14 and crown 16 constructed according to the current state of the art. Implant 10, according to the current state of the art, has a bone apposition surface 17, typically threads or otherwise roughened surface, extending into alveolar bone 18. Abutment-implant interface 12 extends partially into the alveolar bone and has polished surface 20, which is not suitable for bone apposition. Use of implant 10, constructed according to the current state of the art, results in bone-tissue resorption in bone-tissue/soft-tissue transition region 22 because polished surface 20 contacts bone-tissue, which as discussed, leads to bone resorption. Any loss of natural bone structure or topography is highly undesirable from both structural and aesthetic perspectives. Even the smallest bone-tissue loss between the tooth and an implant will lead to soft-tissue shrinkage due to lack of honey support, resulting in "black triangles" (open spaces) between the teeth-a highly unaesthetic situation.

Figure 3:
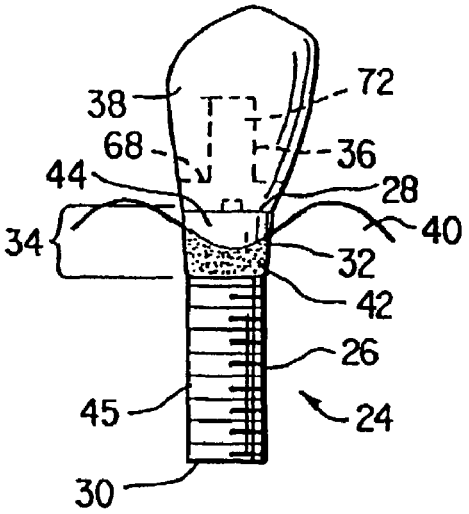
FIG. 3 depicts a frontal view an implant according to an embodiment of the present invention.
Figure 4:
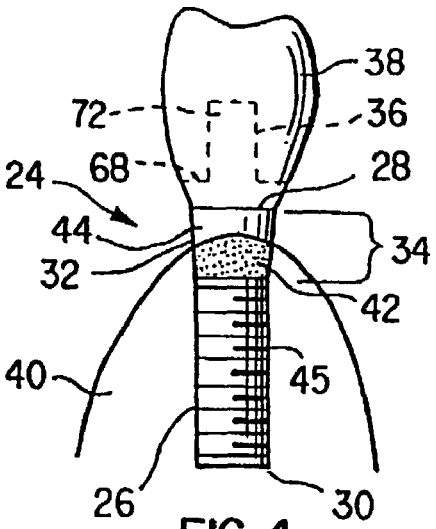
FIG. 4 depicts an interproximal view of the implant in FIG. 3.

FIGS. 3 and 4 show a two-stage implant according to an embodiment of the present invention. Implant 24 has shaft 26, substantially planar abutment-implant interface 28, distal end 30, proximal end 32 and bone-tissue/soft-tissue transition region 34. Abutment 36 and crown 38 are attached to implant 24 using means well known to the skilled artisan for two-stage implants. Implant 24 is made from a biocompatible material, including but not limited to, metal, ceramic, glasses or any combination thereof. Preferably implant 24 is made from titanium or an alloy thereof.

Bone-tissue/soft-tissue transition region 34 has a scalloped bone-tissue apposition surface 42, which approximately follows the naturally occurring contours of existing bone 40, and a scalloped soft-tissue apposition surface 44, which approximately follows the naturally occurring contours of the existing soft-tissue (not shown). Thus, there are two distinctive scalloped tissue-attachment surfaces: bone-tissue apposition surface 42 to maintain the naturally occurring bone-tissue morphology; and soft-tissue apposition surface 44 to maintain the naturally occurring soft-tissue morphology. The degree of scalloping or the height of the convex and concave regions depends on, inter alia, the degree of existing bone-tissue resorption, the size of the implant, the implant location within the arch, the bone morphology and the soft-tissue morphology. The dimensions are similar to the scalloped appearance of the cementoenanel (CE) junction observed on natural teeth. The vertical difference between the highest and lowest point of the scalloped margin ranges from less than 1 mm on posterior teeth to approximately 3-5mm on anterior teeth. By way of example, bone-tissue apposition surface 42 can be obtained by machining, application of textured surfaces, acid etching, blasting with particles, applying growth factor, applying protein, or other materials that promote, enhance, and/or maintain bone-tissue growth and/or apposition. Also by way of example, soft-tissue apposition surface 44 can be achieved by polishing or other treatment that leaves a surface to promote, enhance, and/or maintain soft-tissue growth and/or apposition. Below the bone-tissue/soft-tissue transition region 34, shaft 26 has threads 45, or other means well known in the art, to anchor the implant into the alveolar bone.

In use, the surgeon inserts distal end 30 into the alveolar bone such that bone-tissue apposition surface 42 and soft-tissue apposition surface 44 approximately mirror the existing bone- and soft-tissue morphology respectively. The implant should be aligned such that the highest points of bone apposition surface 42 are substantially aligned with the interproximal areas of the bone-tissue and such that the lowest points are substantially aligned with the buccal and lingual area of the bone-tissue. In a two-stage process, the surgeon sutures tissue over the implant, waits several months for the bone to adhere to the implant, opens the tissue, attaches abutment 36 to abutment-implant interface 28 and attaches crown 38 to abutment 36. Bone-tissue apposition surface 42 and soft-tissue apposition surface 44 maintain bone- and soft-tissue attachment levels and facilitate prevention of peri-implant infections, which occur due to increased peri-implant pocket depths frequently observed with the prior art implant designs. Therefore, implants constructed according to the present invention increase the longevity of the implant and improve the aesthetic appearance of the restoration.

Figure 6:
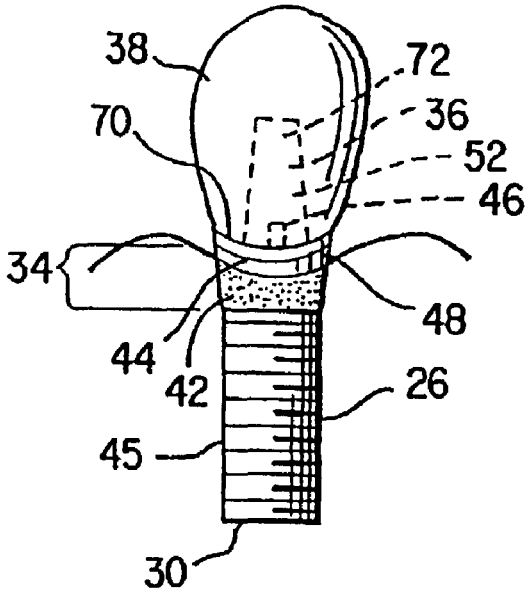
FIG. 6 depicts a frontal view of an implant according to another embodiment of the present invention.
Figure 7:
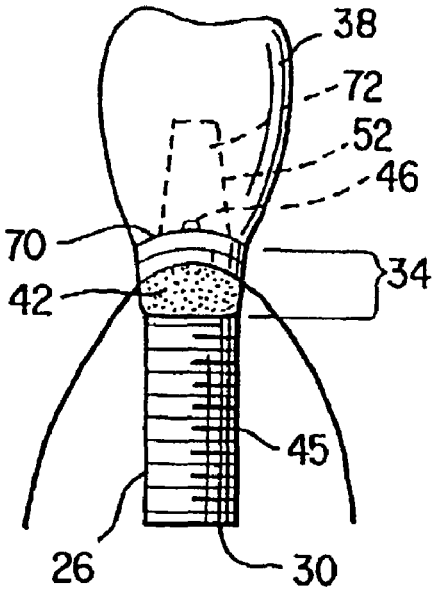
FIG. 7 depicts an interproximal view of the implant in FIG. 6.
Figure 8:
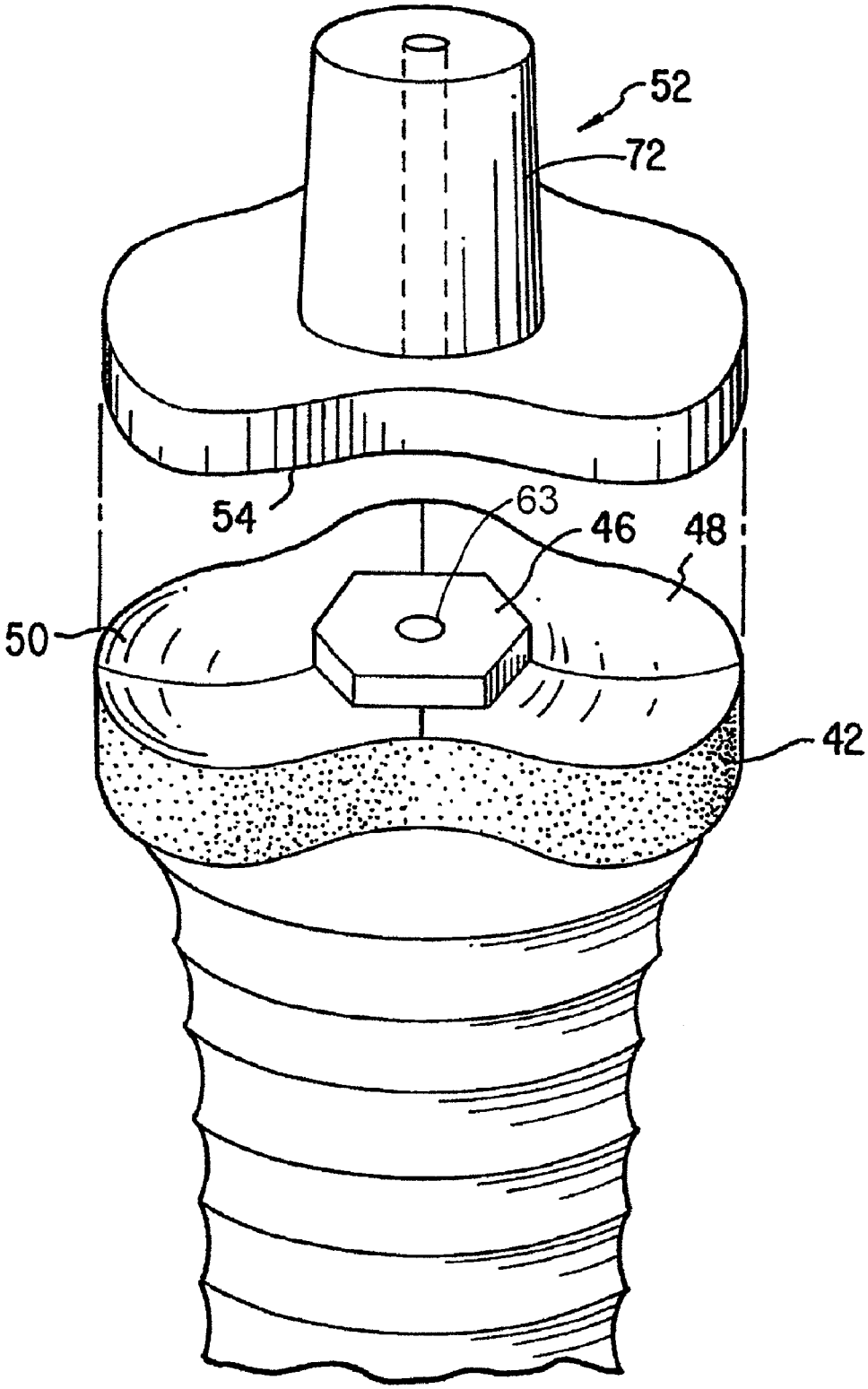
FIG. 8 depicts a three-dimensional top view of the implant in FIG. 6.

Referring to FIGS. 5A and 5B, abutment-implant interface 28 has substantially planar upper surface 25, which is approximately 90° to the longitudinal axis of shaft 26, and connecting means 46 for connecting abutment 36 (FIGS. 3 and 4) to abutment-implant interface 28. *A bore 51 can be provided with an opening on the upper surface of the abutment-implant interface.* Connecting means 46 is well known in the art and includes, but is not limited to, internal hex *55* (*FIG. 5C*), external hex, standard hex, tall hex, wide hex or camlog. In an alternative embodiment of the present invention, as shown in FIGS. 6-8, abutment-implant interface 48 has at least its edges contoured to approximate the contours of the alveolar bone, thereby defining a contoured upper surface 50 (FIG. 8) surrounding connecting means 46. Also provided in this alternative embodiment is abutment 52, which has lower contoured surface 54 configured to substantially mate with contoured upper surface 50. The upper and lower contoured surfaces provide additional lateral support between abutment 52 and abutment-implant interface 48. Additionally, contoured upper surface 48 of this alternative embodiment results in a narrower depth between gum line 54 and abutment-implant interface 48 (FIGS. 6 and 7), thus enhancing longevity of the restoration as a result of decreased pocket depths. *The bore 51 on the abutment-implant interface 48 corresponds with a through bore 63 in the abutment 52.*

Figure 9:
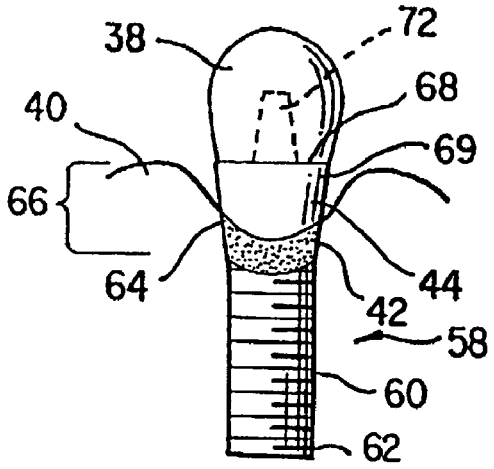
FIG. 9 shows a frontal view of an implant according to another embodiment of the present invention.
Figure 10:
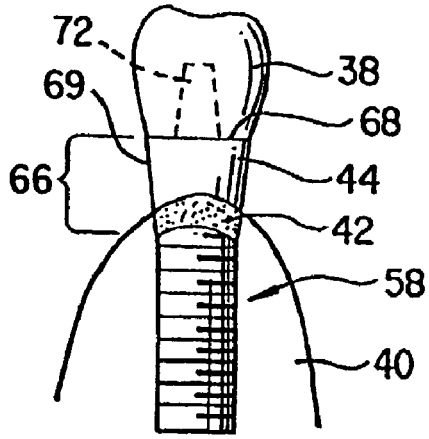
FIG. 10 depicts an interproximal view of the implant in FIG. 9.
Figure 11:
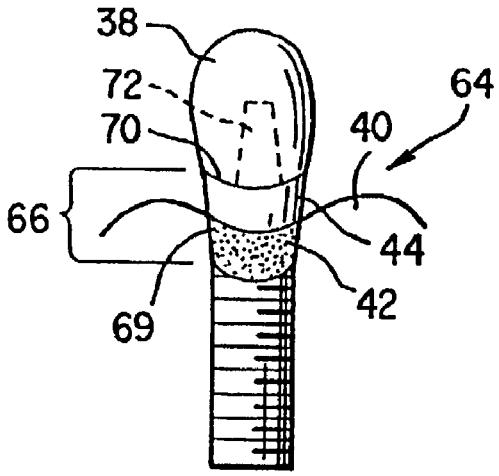
FIG. 11 depicts a frontal view of an implant according to another embodiment of the present invention.
Figure 12:
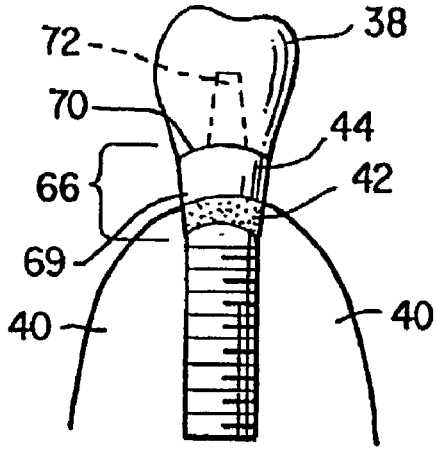
FIG. 12 depicts an interproximal view of the implant in FIG. 11.

A skilled artisan will readily recognize that the principles of the present invention can be equally applied to one-stage as well as two-stage processes. For example, FIGS. 9 and 10 show one-stage implant 58, according to another embodiment of the present invention. Implant 58 includes shaft 60, distal end 62, proximal end 64 and bone-tissue/soft-tissue transition region 66 with scalloped bone-tissue apposition surface 42 and scalloped soft-tissue apposition surface 44, as substantially described above. Abutment 69 is permanently attached to the one-stage implant 58 as is well know in the art.

One-or two-stage implants, according to alternative embodiments of the present invention, may include either a planar abutment-crown interface 68 (FIGS. 3, 4, 9 and 10) or a contoured abutment-crown interface 70 (FIGS. 6, 7, 11 and 12), the latter of which substantially matches the natural contour of the alveolar bone. Contoured abutment-crown interface 70 allows for crown 38, in both one-and two-stage implants, to extend further towards the gum line, thereby resulting in a more aesthetically pleasing restoration. Chimney 72, or other means well known to the skilled artisan, is provided in both one-and two-stage implants according to the present invention for attaching crown 38 to the abutment.

Although various embodiments of the present invention have been described, the descriptions are intended to be merely illustrative. Thus, it will be apparent to the skilled artisan that modifications may be made to the embodiments as described herein without departing from the scope of the claims set forth below.

What is claimed is:

1. An endosseous dental implant, comprising:

a *threaded* shaft made from a biocompatible material, said shaft having a distal end and a proximal end;

an abutment-implant interface disposed towards the proximal end of said shaft; and a bone-tissue apposition surface formed on said shaft and *having an edge* disposed adjacent to said abutment-implant interface, said *edge of the* bone-tissue apposition surface including at least one peak and trough configured to approximate the physiological contours of naturally occurring bone-tissue morphology *and wherein said bone-tissue apposition surface comprises at least one of a roughened surface, a textured surface, or an applied biologic modifier that extends to said edge but does not extend beyond said edge*.

2. The endosseous dental implant according to claim 1, wherein said *edge of the* bone-tissue apposition surface has a non-planar appearance.

3. The endosseous dental implant according to claim 2, wherein *said edge of the bone tissue apposition surface has a highest point and a lowest point and* the highest [points] *point* of said bone-tissue apposition surface *is configured to* substantially [aligns] *align* with the interproximal areas of the bone-tissue, and wherein the lowest [points] *point* of said bone-tissue apposition surface *is configured to* substantially [aligns] *align* with the buccal area of the bone-tissue.

4. The endosseous dental implant according to claim 1 further comprising:

a soft-tissue apposition surface formed on said shaft and disposed between said *edge of the* bone-tissue apposition surface and said abutment-implant interface, said soft-tissue apposition surface *being configured to promote, enhance or maintain soft-tissue growth or apposition and* including *an edge with* at least one peak and trough configured to approximate the physiological contours of naturally occurring soft-tissue morphology.

5. [The endosseous dental implant according to claim 1 further comprising:] *An endosseous dental implant, comprising:*

*a shaft made from a biocompatible material, said shaft having a distal end and a proximal end;*

*an abutment-implant interface disposed towards the proximal end of said shaft;*

*a bone-tissue apposition surface formed on said shaft and having a boundary disposed adjacent to said abutment-implant interface, said boundary of said bone-tissue apposition surface including at least one peak and trough configured to approximate the physiological contours of naturally occurring bone-tissue morphology; and* a means for connecting an abutment to said abutment-implant interface for use in a two-stage procedure*;*

*wherein said bone-tissue apposition surface comprises at least one of a roughened surface, a textured surface, or an applied biologic modifier that extends to said boundary but does not extend beyond said boundary*.

6. The endosseous dental implant according to claim 5, wherein said abutment-implant interface has a substantially planar upper surface approximately 90° to the longitudinal axis of said shaft, and wherein said planar upper surface substantially surrounds said means for connecting.

7. The endosseous dental implant according to claim 5, wherein said abutment-implant interface has a contoured upper surface, and wherein said contoured upper surface substantially surrounds said means for connecting.

8. The endosseous dental implant according to claim 7, further comprising an abutment wherein a lower surface of the abutment substantially abuts against said contoured upper surface, thereby providing improved lateral support.

9. The endosseous dental implant according to claim 1, further comprising:

an abutment permanently attached to said abutment-implant interface for use in a one-stage procedure.

[10. The endosseous dental implant according to claim 9, wherein said shaft and said abutment are constructed from a single piece of material.]

11. The endosseous dental implant according to claim 9, wherein said abutment has a substantially planar upper surface approximately 90° to the longitudinal axis of said shaft and wherein said planar upper surface substantially surrounds a chimney.

12. The endosseous dental implant according to claim 9, wherein said abutment has a contoured upper surface and wherein said contoured upper surface substantially surrounds a chimney.

13. A one-stage endosseous dental implant, comprising:

a *threaded* shaft made from a biocompatible material, said shaft having a distal end and a proximal end;

a bone-tissue apposition surface formed on said shaft and *comprising an edge* disposed adjacent to [said] *an* abutment-implant interface, said *edge of said* bone-tissue apposition surface including at least one peak and trough configured to approximate the physiological contours of naturally occurring bone-tissue morphology; and an abutment permanently attached to the proximal end of said shaft*;*

*wherein said bone-tissue apposition surface comprises at least one of a roughened surface, a textured surface, or an applied biologic modifier that extends to said edge but does not extend beyond said edge*.

14. The one-stage endosseous dental implant according to claim 13, wherein said abutment has a substantially planar upper surface approximately 90° to the longitudinal axis of said shaft, and wherein said planar upper surface substantially surrounds a chimney.

15. The one-stage endosseous dental implant according to claim 13, wherein said abutment has a contoured upper surface and wherein said contoured upper surface substantially surrounds a chimney.

16. A two-stage endosseous dental implant system, comprising:

a shaft made from a biocompatible material, said shaft having a distal end and a proximal end;

a bone-tissue apposition surface formed on said shaft and *an edge* disposed adjacent to [said] *an* abutment-implant interface, said *edge of said* bone-tissue apposition surface including at least one peak and trough configured to approximate the physiological contours of naturally occurring bone-tissue morphology*, wherein said bone-tissue apposition surface comprises at least one of a roughened surface, a textured surface, or an applied biologic modifier that extends to said edge but does not extend beyond said edge*;

an abutment-implant interface disposed towards the proximal end of said shaft;

an abutment configured to attach to said abutment-implant interface;

a means for connecting said abutment to said *shaft* abutment-implant interface; and a crown having a distal end configured to fit over said abutment.

17. The two-stage endosseous dental implant system according to claim 16, wherein said abutment-implant interface has a substantially planar upper surface substantially surrounding [said means for connecting] *a bore*, and wherein said upper planar surface is approximately 90° to the longitudinal axis of said shaft.

18. The two-stage endosseous dental implant system according to claim 17, wherein said abutment has a substantially planar upper abutment-crown interface surface.

19. The two-stage endosseous dental implant system according to claim 17, wherein said abutment has a contoured upper abutment-crown interface surface substantially surrounding a chimney, and wherein a distal end of said crown is configured such that at least an outside surface of said crown extends to and follows the contours of said upper abutment-crown interface surface, thereby providing a narrow depth between the distal end of said crown and said bone tissue apposition surface.

20. The two-stage endosseous dental implant system according to claim 16, wherein said abutment-implant interface has a contoured upper surface substantially surrounding [said means for connecting] *a bore*, and said contoured upper surface approximately matches the contour of the natural bone morphology, and wherein said abutment has a lower surface configured to substantially abut said contoured upper surface.

21. The two-stage endosseous dental implant system according to claim 20, wherein said abutment has a substantially planar upper abutment-crown interface surface.

22. The two-stage endosseous dental implant system according to claim 20, wherein said abutment has a contoured upper abutment-crown interface surface substantially surrounding a chimney, and wherein a distal end of said crown is configured such that at least an outside surface of said crown extends to and follows the contours of said upper abutment-crown interface surface, thereby providing a narrow depth between the distal end of said crown and said bone-tissue apposition surface.

23. A one-stage endosseous dental implant system, comprising:

a *threaded* shaft made from a biocompatible material, said shaft having a distal end and a proximal end;

a bone-tissue apposition surface formed on said shaft and *comprising an edge* disposed adjacent to [said] *an* abutment-implant interface, said *edge of said* bone-tissue apposition surface including at least one peak and trough configured to approximate the physiological contours of naturally occurring bone-tissue morphology;

an abutment permanently attached to the proximal end of said shaft; and a crown having a distal end configured to secure to said abutment*;*

*wherein said bone-tissue apposition surface comprises at least one of a roughened surface, a textured surface, or an applied biologic modifier that extends to said edge but does not extend beyond said edge*.

24. The one-stage endosseous dental implant system according to claim 23, wherein said abutment has a substantially planar upper surface substantially surrounding a chimney, and wherein said upper planar surface is approximately 90° to the longitudinal axis of said shaft.

25. The one-stage endosseous dental implant system according to claim 23, wherein said abutment has a contoured upper surface substantially surrounding a chimney, and wherein said contoured upper surface approximately matches the contour of naturally occurring bone-tissue morphology.

26. The one-stage endosseous dental implant system according to claim 25, wherein a distal end of said crown is configured such that at least an outside surface of said crown extends to and follows the contours of said contoured upper surface, thereby providing a narrow depth between the distal end of said crown and the bone-tissue apposition surface.

*27. The endosseous dental implant according to claim 4, wherein said soft-tissue apposition surface comprises a polished surface.*

*28. The endosseous dental implant according to claim 1, further comprising:*

*an anti-rotational feature and a bore for connecting an abutment to said abutment-implant interface for use in a two-stage procedure.*

*29. The endosseous dental implant according to claim 28, wherein said abutment-implant interface has a substantially planar upper surface approximately 90° to the longitudinal axis of said shaft, and wherein said planar upper surface substantially surrounds said bore.*

*30. The endosseous dental implant according to claim 28, wherein said abutment-implant interface has a contoured upper surface, and wherein said contoured upper surface substantially surrounds said bore.*

*31. The endosseous dental implant according to claim 30, further comprising an abutment wherein a lower surface of the abutment substantially abuts against said contoured upper surface, thereby providing improved lateral support.*

*32. The endosseous dental implant according to claim 1, wherein said bone-tissue apposition surface comprises an applied textured surface.*

*33. The endosseous dental implant according to claim 1, wherein said bone-tissue apposition surface comprises an applied growth factor.*

*34. The endosseous dental implant according to claim 1, wherein said bone-tissue apposition surface comprises an applied protein.*

*35. The endosseous dental implant according to claim 1, wherein said bone-tissue apposition surface comprises an acid etched surface.*

*36. The endosseous dental implant according to claim 1, wherein said bone-tissue apposition surface comprises a surface blasted with particles.*

*37. The endosseous dental implant according to claim 1, wherein said edge of said bone-tissue apposition surface includes a set of peaks and troughs.*

*38. The endosseous dental implant according to claim 1, wherein said edge of said bone-tissue apposition surface includes two peaks and two troughs.*

*39. The endosseous dental implant according to claim 5, wherein said bone-tissue apposition surface comprises an applied textured surface.*

*40. The endosseous dental implant according to claim 5, wherein said bone-tissue apposition surface comprises an applied growth factor.*

*41. The endosseous dental implant according to claim 5, wherein said bone-tissue apposition surface comprises an applied protein.*

*42. The endosseous dental implant according to claim 5, wherein said bone-tissue apposition surface comprises an acid etched surface.*

*43. The endosseous dental implant according to claim 5, wherein said bone-tissue apposition surface comprises a surface blasted with particles.*

*44. The endosseous dental implant according to claim 5, wherein said boundary of said bone-tissue apposition surface defines a set of peaks and troughs.*

*45. The endosseous dental implant according to claim 5, wherein an edge of said bone-tissue apposition surface defines two peaks and two troughs.*

*46. The endosseous dental implant according to claim 45, further comprising a soft-tissue apposition surface formed on said shaft and disposed between said edge of said bone-tissue apposition surface and said abutment-implant interface, said soft-tissue apposition surface including an edge with at least two peaks and troughs configured to approximate the physiological contours of naturally occurring soft-tissue morphology, said soft-tissue apposition surface being configured to promote, enhance or maintain soft-tissue growth or apposition.*

*47. The endosseous dental implant according to claim 5, further comprising a soft-tissue apposition surface formed on said shaft and disposed between said edge of said bone-tissue apposition surface and said abutment-implant interface, said soft-tissue apposition surface including an edge with at least one peak and trough configured to approximate the physiological contours of naturally occurring soft-tissue morphology, said soft-tissue apposition surface being configured to promote, enhance or maintain soft-tissue growth or apposition.*

*48. The endosseous dental implant according to claim 5, further comprising a soft-tissue apposition surface formed on said shaft and disposed between said edge of said bone-tissue apposition surface and said abutment-implant interface, said soft-tissue apposition surface being configured to promote, enhance or maintain soft-tissue growth or apposition.*

*49. The one-stage endosseous dental implant according to claim 13, wherein said abutment has a substantially planar upper surface approximately 90° to the longitudinal axis of said shaft.*

*50. The one-stage endosseous dental implant according to claim 13, wherein said abutment has a contoured upper surface.*

*51. The endosseous dental implant according to claim 13, wherein said bone-tissue apposition surface comprises an applied textured surface.*

*52. The endosseous dental implant according to claim 13, wherein said bone-tissue apposition surface comprises an applied growth factor.*

*53. The endosseous dental implant according to claim 13, wherein said bone-tissue apposition surface comprises an applied protein.*

*54. The endosseous dental implant according to claim 13, wherein said bone-tissue apposition surface comprises an acid etched surface.*

*55. The endosseous dental implant according to claim 13, wherein said bone-tissue apposition surface comprises a surface blasted with particles.*

*56. The endosseous dental implant according to claim 13, wherein said edge of said bone-tissue apposition surface includes a set of peaks and troughs.*

*57. The endosseous dental implant according to claim 13, wherein said edge of said bone-tissue apposition surface includes two peaks and two troughs.*

*58. The endosseous dental implant according to claim 57, further comprising a soft-tissue apposition surface formed on said shaft and disposed between said edge of said bone-tissue apposition surface and said abutment-implant interface, said soft-tissue apposition surface including an edge with at least two peaks and troughs configured to approximate the physiological contours of naturally occurring soft-tissue morphology, said soft-tissue apposition surface being configured to promote, enhance or maintain soft-tissue growth or apposition.*

*59. The endosseous dental implant according to claim 13, further comprising a soft-tissue apposition surface formed on said shaft and disposed between said edge of said bone-tissue apposition surface and said abutment-implant interface, said soft-tissue apposition surface including an edge with at least one peak and trough configured to approximate the physiological contours of naturally occurring soft-tissue morphology, said soft-tissue apposition surface being configured to promote, enhance or maintain soft-tissue growth or apposition.*

*60. The endosseous dental implant according to claim 13, further comprising a soft-tissue apposition surface formed on said shaft and disposed between said edge of said bone-tissue apposition surface and said abutment-implant interface, said soft-tissue apposition surface being configured to promote, enhance or maintain soft-tissue growth or apposition.*

*61. The two-stage endosseous dental implant system according to claim 16, further comprising an anti-rotational member on said shaft for connecting said abutment to said shaft, wherein said anti-rotational feature is an external hex.*

*62. The two-stage endosseous dental implant system according to claim 16, wherein said abutment includes a through-bore.*

*63. An endosseous dental implant, comprising:*

*a shaft made from a biocompatible material, said shaft having a distal end and a proximal end;*

*an upper surface disposed towards the proximal end of said shaft;*

*a bone-tissue apposition surface formed on said shaft and said bone-tissue apposition surface having an edge including at least one peak and trough configured to approximate the physiological contours of naturally occurring bone-tissue morphology, wherein said bone-tissue apposition surface comprises at least one of a roughened surface, a textured surface, or an applied biologic modifier that extends to said edge but does not extend beyond said edge;*

*a bore having an opening on said upper surface for connecting an abutment to said shaft; and*

*an anti-rotational member on said shaft also for connecting an abutment to said shaft.*

*64. The endosseous dental implant of claim 63, wherein said anti-rotational member is an external hex.*

*65. The endosseous dental implant of claim 63, wherein said anti-rotational member is an internal hex formed in said upper surface.*

*66. The endosseous dental implant of claim 63, wherein said upper surface is substantially planar and approximately 90° to the longitudinal axis of said shaft.*

*67. The endosseous dental implant of claim 63, wherein said upper surface is contoured.*

*68. The endosseous dental implant of claim 67, wherein said shaft includes threads.*

*69. The endosseous dental implant of claim 67, further comprising a soft-tissue apposition surface formed on said shaft and disposed between said edge of said bone-tissue apposition surface and said upper surface, said soft-tissue apposition surface including an edge with at least one peak and trough configured to approximate the physiological contours of naturally occurring soft-tissue morphology, and said soft-tissue apposition surface being configured to promote, enhance or maintain soft-tissue growth or apposition.*

*70. The endosseous dental implant according to claim 69, wherein said soft-tissue apposition surface comprises a polished surface.*

*71. The endosseous dental implant of claim 63, wherein the shaft includes threads.*

*72. The endosseous dental implant of claim 63, further comprising a soft-tissue apposition surface formed on said shaft and disposed between said edge of said bone-tissue apposition surface and said upper surface, said soft-tissue apposition surface including an edge with at least one peak and trough configured to approximate the physiological contours of naturally occurring soft-tissue morphology, and said soft-tissue apposition surface being configured to promote, enhance or maintain soft-tissue growth or apposition.*

*73. The endosseous dental implant according to claim 72, wherein said soft-tissue apposition surface comprises a polished surface.*

*74. The endosseous dental implant according to claim 63, wherein said bone-tissue apposition surface comprises an applied textured surface.*

*75. The endosseous dental implant according to claim 63, wherein said bone-tissue apposition surface comprises an applied growth factor.*

*76. The endosseous dental implant according to claim 63, wherein said bone-tissue apposition surface comprises an applied protein.*

*77. The endosseous dental implant according to claim 63, wherein said bone-tissue apposition surface comprises an acid etched surface.*

*78. The endosseous dental implant according to claim 63, wherein said bone-tissue apposition surface comprises a surface blasted with particles.*

*79. The endosseous dental implant according to claim 63, wherein said edge of said bone-tissue apposition surface includes a set of peaks and troughs.*

*80. The endosseous dental implant according to claim 63, wherein said edge of said bone-tissue apposition surface includes two peaks and two troughs.*

*81. The endosseous dental implant according to claim 80, further comprising a soft-tissue apposition surface formed on said shaft and disposed between said edge of said bone-tissue apposition surface and an abutment-implant interface, said soft-tissue apposition surface including an edge with at least two peaks and troughs configured to approximate the physiological contours of naturally occurring soft-tissue morphology, said soft-tissue apposition surface being configured to promote, enhance or maintain soft-tissue growth or apposition.*

*82. The endosseous dental implant according to claim 63, further comprising a soft-tissue apposition surface formed on said shaft and disposed between said edge of said bone-tissue apposition surface and an abutment-implant interface, said soft-tissue apposition surface including at least one peak and trough configured to approximate the physiological contours of naturally occurring soft-tissue morphology, said soft-tissue apposition surface being configured to promote, enhance or maintain soft-tissue growth or apposition.*

*83. The endosseous dental implant according to claim 63, further comprising a soft-tissue apposition surface formed on said shaft and disposed between said edge of said bone-tissue apposition surface and a abutment-implant interface, said soft-tissue apposition surface being configured to promote, enhance or maintain soft-tissue growth or apposition.*

*84. An endosseous dental implant, comprising:*

*a shaft made from a biocompatible material, said shaft having a distal end and a proximal end, said shaft being substantially symmetrical about a straight longitudinal axis of said shaft;*

*an upper surface disposed towards the proximal end of said shaft;*

*a bone tissue/soft tissue transition region between said shaft and said upper surface; and*

*a bone-tissue apposition surface formed on said bone tissue/soft tissue transition region, said bone-tissue apposition surface comprising an edge with at least one peak and trough configured to approximate the physiological contours of naturally occurring bone-tissue morphology, wherein said bone-tissue apposition surface comprises at least one of a roughened surface, a textured surface, or an applied biologic modifier that extends to said edge but does not extend beyond said edge.*

*85. The endosseous dental implant according to claim 84, wherein said edge of said bone tissue apposition surface has a highest point and a lowest point and the highest point of said edge of said bone-tissue apposition surface substantially aligns with the interproximal areas of the bone-tissue, and wherein the lowest point of said edge of said bone-tissue apposition surface substantially aligns with the buccal area of the bone-tissue.*

*86. The endosseous dental implant according to claim 84 further comprising:*

*a soft-tissue apposition surface formed on said shaft and disposed between said bone-tissue apposition surface and said upper surface, said soft-tissue apposition surface having an edge including at least one peak and trough configured to approximate the physiological contours of naturally occurring soft-tissue morphology.*

*87. The endosseous dental implant according to claim 86, wherein said soft-tissue apposition surface comprises a polished surface.*

*88. The endosseous dental implant according to claim 84, wherein said upper surface has a substantially planar upper surface approximately 90° to the longitudinal axis of said shaft.*

*89. The endosseous dental implant according to claim 84, wherein upper surface has a contoured upper surface.*

*90. The endosseous dental implant according to claim 84, further comprising:*

*an abutment permanently attached to said upper surface for use in a one-stage procedure.*

*91. The endosseous dental implant according to claim 90, wherein said shaft and said abutment are constructed from a single piece of material.*

*92. The endosseous dental implant according to claim 90, wherein said abutment has a substantially planar upper surface approximately 90° to the longitudinal axis of said shaft.*

*93. The endosseous dental implant according to claim 90, wherein said abutment has a contoured upper surface.*

*94. The endosseous dental implant according to claim 84, further comprising a bore having an opening on said upper surface for connecting an abutment to said shaft and an anti-rotational member comprising a plurality of interconnected sides also for connecting an abutment to said shaft.*

*95. The endosseous dental implant according to claim 94, wherein said anti-rotational member is an external hex.*

*96. The endosseous dental implant according to claim 94, wherein said anti-rotational member is an internal hex.*

*97. The endosseous dental implant according to claim 84, wherein said bone-tissue apposition surface comprises an applied textured surface.*

*98. The endosseous dental implant according to claim 84, wherein said bone-tissue apposition surface comprises an applied growth factor.*

*99. The endosseous dental implant according to claim 84, wherein said bone-tissue apposition surface comprises an applied protein.*

*100. The endosseous dental implant according to claim 84, wherein said bone-tissue apposition surface comprises an acid etched surface.*

*101. The endosseous dental implant according to claim 84, wherein said bone-tissue apposition surface comprises a surface blasted with particles.*

*102. The endosseous dental implant according to claim 84, wherein said edge of said bone-tissue apposition surface includes a set of peaks and troughs.*

*103. The endosseous dental implant according to claim 102, further comprising a soft-tissue apposition surface formed on said shaft and disposed between said edge of said bone-tissue apposition surface and a abutment-implant interface, said soft-tissue apposition surface including at least two peaks and troughs configured to approximate the physiological contours of naturally occurring soft-tissue morphology, said soft-tissue apposition surface being configured to promote, enhance or maintain soft-tissue growth or apposition.*

*104. The endosseous dental implant according to claim 84, further comprising a soft-tissue apposition surface formed on said shaft and disposed between said edge of said bone-tissue apposition surface and said abutment-implant interface, said soft-tissue apposition surface including at least one peak and trough configured to approximate the physiological contours of naturally occurring soft-tissue morpholoogy, said soft-tissue apposition surface being configured to promote, enhance or maintain soft-tissue growth or apposition.*

*105. The endosseous dental implant according to claim 84, further comprising a soft-tissue apposition surface formed on said shaft and disposed between said edge of said bone-tissue apposition surface and said abutment-implant interface, said soft-tissue apposition surface being configured to promote, enhance or maintain soft-tissue growth or apposition.*

*106. The endosseous dental implant according to claim 84, wherein said edge of said bone-tissue apposition surface includes two peaks and two troughs.*

* * * * *